(12) United States Patent
Lingenhöle et al.

(10) Patent No.: US 7,217,129 B2
(45) Date of Patent: May 15, 2007

(54) MEDICAL OR DENTAL-MEDICAL HANDPIECE HAVING AT LEAST ONE ROTARY PART

(75) Inventors: Bernhard Lingenhöle, Warthausen (DE); Eugen Eibofner, Biberach (DE); Bernhard Kuhn, Biberach (DE)

(73) Assignee: Kaltenbach & Voigt GmbH & Co. KG, Biberach (DE)

( * ) Notice: Subject to any disclaimer, the term of this patent is extended or adjusted under 35 U.S.C. 154(b) by 446 days.

(21) Appl. No.: 10/428,058

(22) Filed: Apr. 28, 2003

(65) Prior Publication Data

US 2003/0207233 A1 Nov. 6, 2003

Related U.S. Application Data

(63) Continuation of application No. PCT/EP02/09603, filed on Aug. 28, 2002.

(30) Foreign Application Priority Data

Aug. 28, 2001 (EP) ................... 01120523

(51) Int. Cl.
*A61C 1/05* (2006.01)
*F16C 19/08* (2006.01)

(52) U.S. Cl. .................................... 433/132

(58) Field of Classification Search ............. 433/120, 433/131, 132; 384/504, 512, 613, 619
See application file for complete search history.

(56) References Cited

U.S. PATENT DOCUMENTS

| | | | | |
|---|---|---|---|---|
| 1,379,645 A | * | 5/1921 | Moore | 82/117 |
| 1,495,564 A | * | 5/1924 | Vincon | 384/504 |
| 1,703,380 A | * | 2/1929 | Beemer | 384/477 |
| 2,180,993 A | * | 11/1939 | Monnier | 415/91 |
| 2,227,697 A | * | 1/1941 | Blood | 451/155 |
| 2,651,554 A | * | 9/1953 | Recknagel | 384/504 |
| 3,092,908 A | * | 6/1963 | Flatland | 433/92 |
| 3,376,084 A | | 4/1968 | McKee | 308/184 |
| 3,731,384 A | * | 5/1973 | Brooks et al. | 433/32 |
| 4,021,919 A | * | 5/1977 | Lingenhole et al. | 433/132 |
| 4,071,954 A | | 2/1978 | Eibofner | 32/27 |
| 4,408,808 A | * | 10/1983 | Redmann et al. | 384/473 |
| 4,411,479 A | | 10/1983 | Hirata et al. | 308/195 |
| 4,470,813 A | * | 9/1984 | Thorburn | 433/132 |
| 5,826,989 A | * | 10/1998 | Obara et al. | 384/613 |
| 6,050,728 A | * | 4/2000 | Obara et al. | 384/613 |
| 6,152,736 A | * | 11/2000 | Schmidinger et al. | 433/132 |
| 6,309,109 B1 | * | 10/2001 | Chuang | 384/537 |
| 2003/0138173 A1 | * | 7/2003 | Herles et al. | 384/92 |

FOREIGN PATENT DOCUMENTS

| | | |
|---|---|---|
| DE | 26 18 739 | 11/1977 |
| DE | 93 07 903.6 | 9/1993 |
| FR | 2 336 590 | 8/1977 |

* cited by examiner

Primary Examiner—Todd E. Manahan
(74) Attorney, Agent, or Firm—Marshall, Gerstein & Borun LLP

(57) ABSTRACT

The invention relates to a medical or dental-medical handpiece having a rotary part, in particular a turbine rotor. In order to improve the handpiece with regard to small construction, running noise and economical construction, there is provided a roller bearing for the purpose of mounting the rotary part, having at least two roller body rows arranged next to one another.

7 Claims, 4 Drawing Sheets

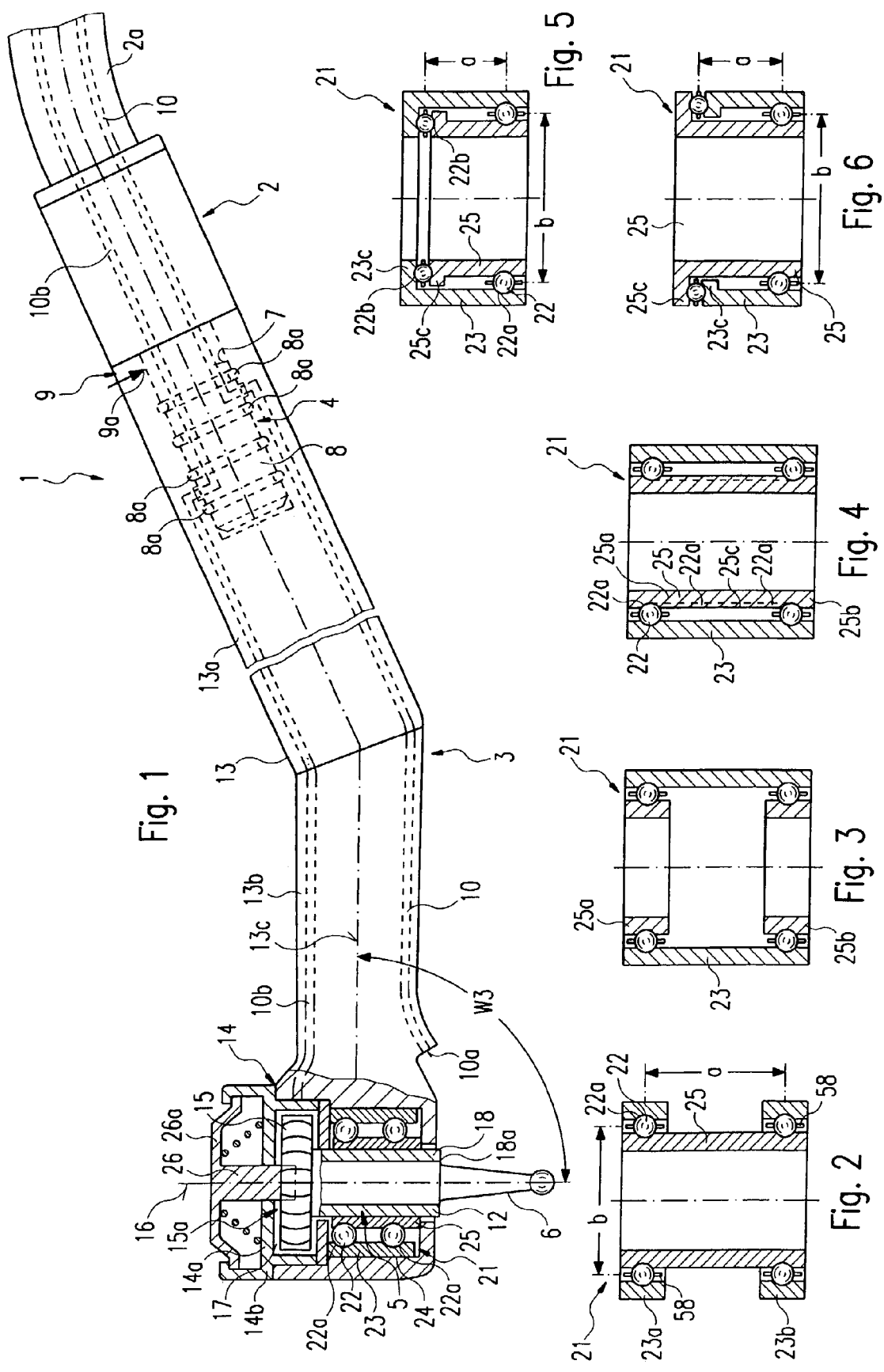

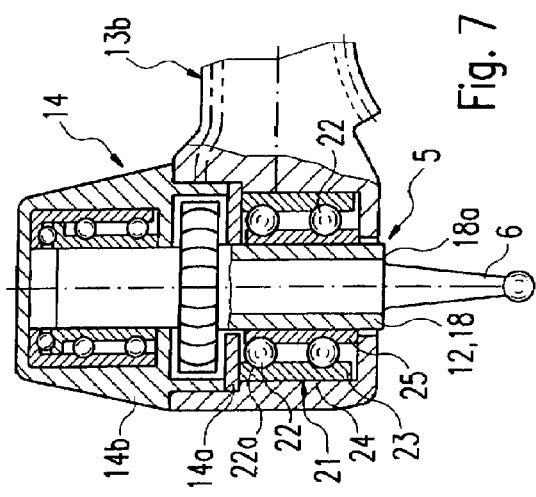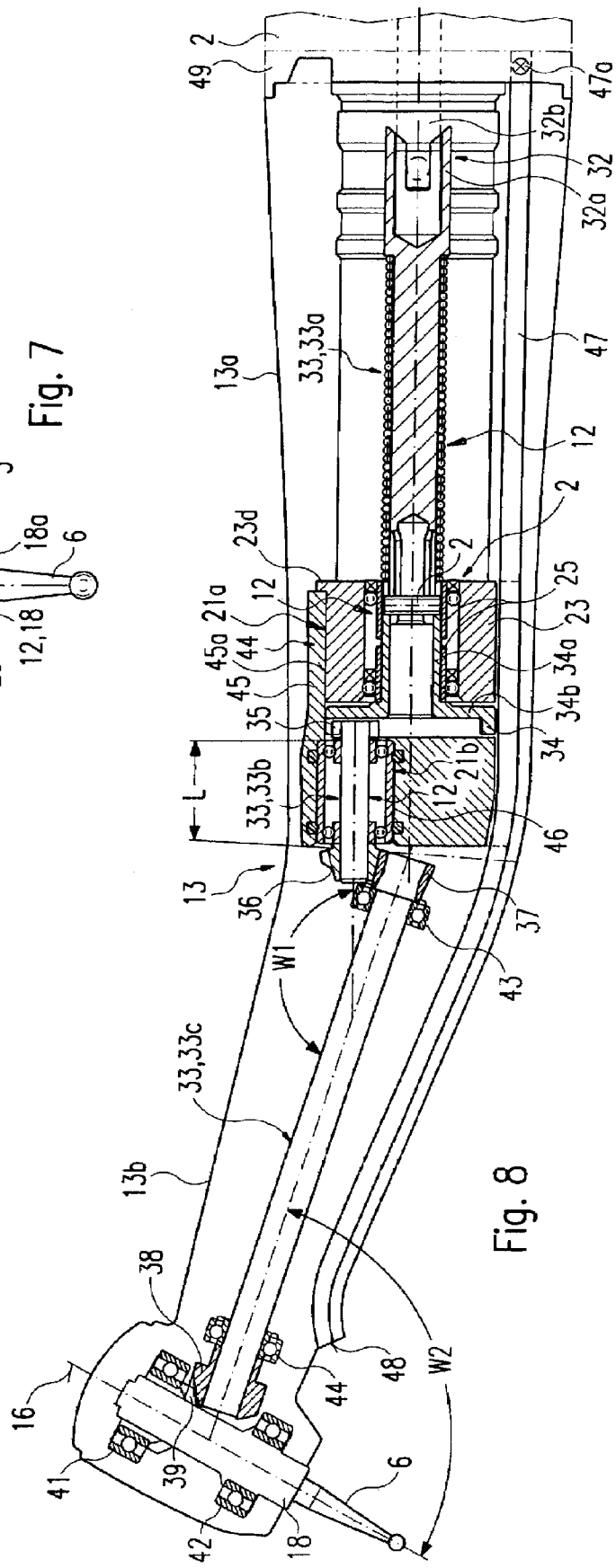

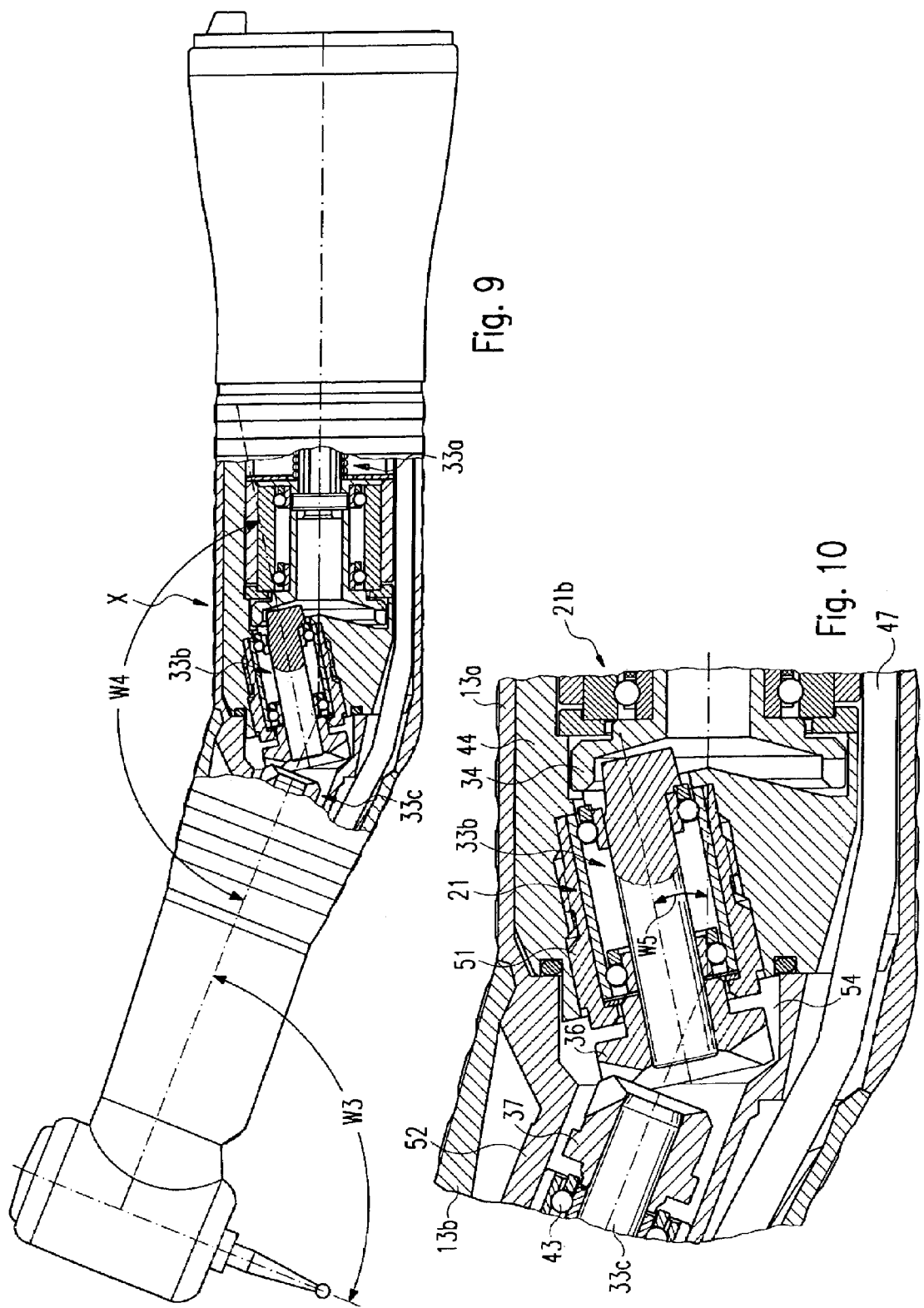

MEDICAL OR DENTAL-MEDICAL HANDPIECE HAVING AT LEAST ONE ROTARY PART

Figure 11:
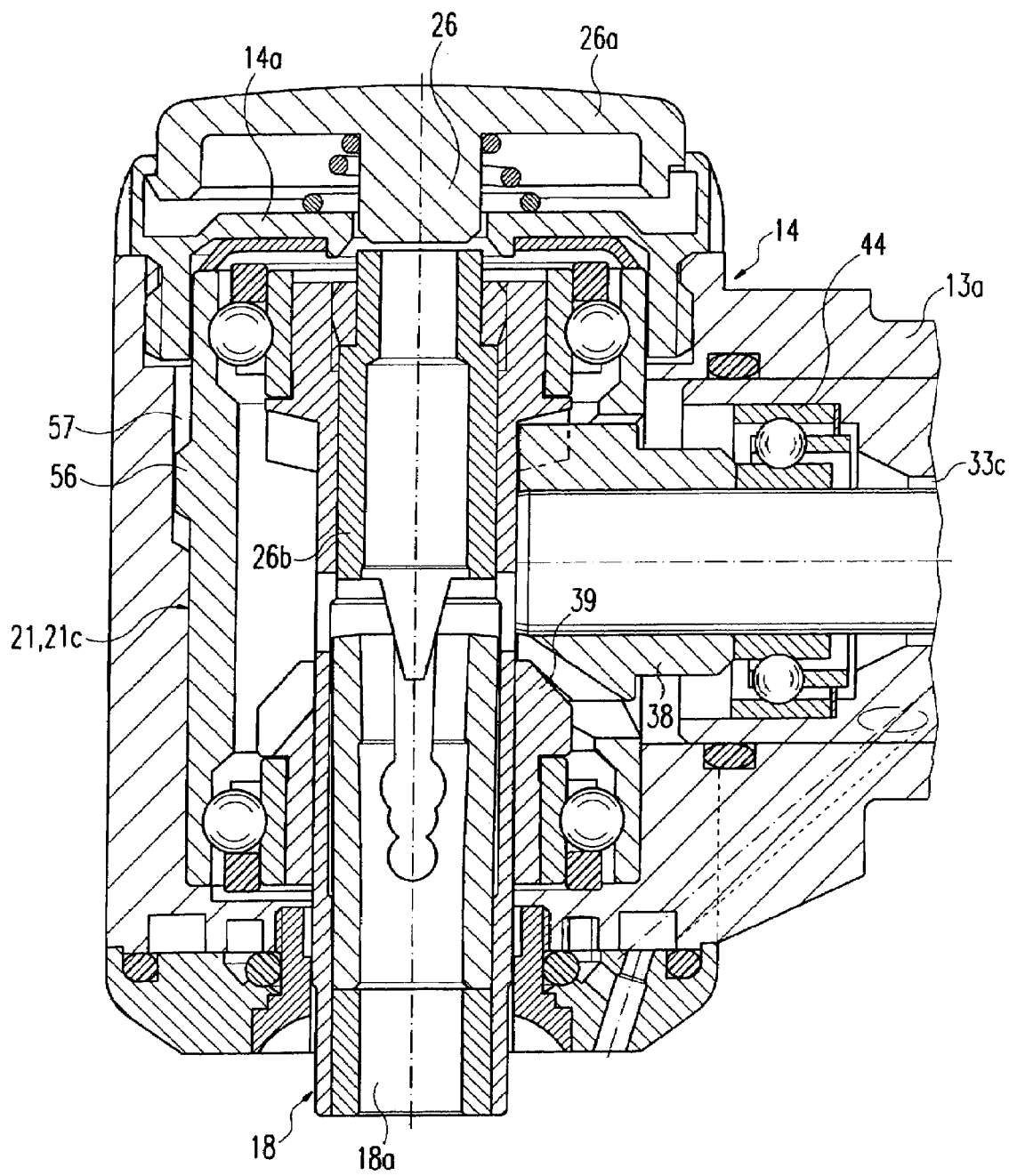

This is a continuation of International Application No. PCT/EP02/09603 filed Aug. 28, 2002, the entire disclosure of which is incorporated herein by reference.

The invention relates to a medical or dental-medical handpiece or to a roller bearing for such a handpiece.

In the case of a handpiece of the kind concerned here there is involved an elongate or rod-shaped object which has in its forward end region a tool for the treatment of the human or animal body or of a model (prosthesis) thereof, or which is connectable with such a tool, and at its rearward end it is connected, or is connectable by means of a coupling, with a so-called flexible supply line. Through the supply line there can be delivered to the handpiece drive energy for a drive motor and/or supply energy, e.g. for a lighting device, and/or treatment media.

Handpieces of the kind concerned here exist in various configurations with regard to shaping and construction, the kind of tool and tool movement and/or the kind of drive. There are handpieces in the shape of a grip part extending straight or angled. In the case of the tool there is involved e.g. a rotary tool or a tool which can be moved back and forth. As drive, the handpiece may be configured with a mechanical drive having a rotatably mounted drive shaft or a pneumatic drive with a turbine arranged preferably in the forward handpiece region, to which a compressed air line extends forwardly from the rear.

A handpiece of the kind concerned here can thus have in any region of its length a rotatably mounted rotary part which is configured for functional operation from high speed to low speed. A high speed functional operation is employed in the most cases for a tool for material removing working, e.g. for the removal of caries. There are, however, also handpieces having a tool which is driven with lesser speed of rotation, e.g. in the case of such tools which in functional operation carry out a screwing operation, as is the case with implantation for the placing and removal of implants.

A handpiece in accordance with the preamble of claim 1 is described for example in DE-OS 26 18 739. Here there is involved a so-called turbine angled piece the turbine rotor of which is rotatably mounted by means of two ball bearings which are located to the two sides of a turbine wheel of the turbine rotor.

A handpiece of the kind concerned here must meet several requirements. In particular in the case of a handpiece for or with a tool which in functional operation rotates at high speed there is a need for improvement with regard to the noise caused, since a noisy operation disturbs the patient to be treated. This applies in particular for handpieces which are used in the head region of the patient, as is the case with dental-medical handpieces.

In order to obtain a structural size which is suitable for the hand, but otherwise can also be put to use in small body cavities, a handpiece of the kind concerned should also be of a small manner of construction, which relates also to the rotary part and its bearing parts. Here it is also to be taken into account that whilst ensuring a small manner construction a simple and rapidly effectible assembly and disassembly should be possible.

On the other hand, for improving its chances in the marketplace, the handpiece should be of economical construction.

The object of the invention is to improve a handpiece or a roller bearing with regard to the above-described requirements.

With the configuration in accordance with the invention, the handpiece has at least one roller bearing, in particular a miniature roller bearing, whose purpose is to mount the rotary part, the roller bearing having at least two roller body rows arranged next to one another. The inner ring and/or the outer ring extend in each case axially over both roller bearing rows. Through this there are achieved several advantages. On the one hand the roller bearing is stabilized by the bearing sleeve or sleeves extending over both roller bearing rows. This leads to a lesser loading of the roller bearing and to a smooth rotational operation of longer working life. Thereby it has also been determined that the running noises arising in functional operation are reduced, which is significant in particular for high speed roller bearings or rotary parts. A configuration in accordance with the invention also leads to lesser production costs, since the roller bearing in accordance with the invention can replace two individual roller bearings and due to the manner of construction with a common inner and/or outer bearing sleeve two parts are connected with one another to a common part and thus this common part can be produced more economically. The connection to a common part or to a common structural unit also makes possible a simple and rapid assembly, since fewer components have to be handled.

A roller bearing of the kind concerned has in functional operation to take up not only radial load forces but also axial load forces, which can then appear more strongly when the tool is exposed to axial loads in functional operation.

The invention thus has further the object of improving a roller bearing with regard to its suitability to take up also axial load forces.

With the roller bearing according to one embodiment of the invention a roller body row can take up axial load forces. Thus, the roller bearing in accordance with the invention can be put to use both in cases in which radial loads arise and also in cases in which axial loads arise. Here it is to be seen as a further advantage that a radial bearing and an axial bearing are integrated in one roller bearing unit, whereby production costs, structural sizes, bearing capacities and the effort involved in assembly and disassembly can be reduced.

This improvement can be realized with simpler and less expensive manner of construction of the roller bearing, through which the competitiveness of the roller bearing and of the handpiece is also improved.

With a handpiece in which a drive shaft chain for the drive of the tool is rotatably mounted there arise particular requirements in the forward end region of a tool receiver extending transversely of the longitudinal axis of the handpiece and/or in the apex region of an angled handpiece, taking into account desired speeds of rotation and/or the directions of rotation.

The invention thus has a further object of improving a handpiece with respect to the drive shaft sections standing in driving connection with one another.

With the configuration according to another embodiment of the invention the handpiece has a further drive shaft section, namely a middle drive shaft section, which makes it possible to reverse the direction of rotation of the forward drive shaft section and/or to realize gearing up or gearing down of speeds of rotation. Through this the handpiece can be so modified that it can meet special requirements or a greater range of requirements, and thus the range of applications of the handpiece is increased.

Other features further contribute to a small, economically producible, stable, advantageously integratable and stabilizing manner of construction of reliable functioning and long working life.

Below, advantageous configuration of the invention will be described in more detail with reference to the drawings. There is shown:

FIG. 1 a handpiece in accordance with the invention having a rotary part which is mounted in a roller bearing, in a side view, partially sectioned;

FIG. 2 a roller bearing in a modified configuration, as an individual part, in axial section;

FIG. 3 a roller bearing, in axial section, in a modified configuration;

FIG. 4 a roller bearing, in axial section, in a further modified configuration;

FIG. 5 a roller bearing in accordance with the invention, in axial section, in a further modified configuration;

FIG. 6 a roller bearing in accordance with the invention, in axial section, in a further modified configuration;

FIG. 7 the forward end region of the handpiece, in axial section, in a further modified configuration;

FIG. 8 a handpiece in accordance with the invention, in axial section, a in further modified configuration;

FIG. 9 a handpiece in accordance with the invention, in axial section, in a further modified configuration;

FIG. 10 the detail designated by X in FIG. 9, in an illustration to an enlarged scale;

FIG. 11 the forward end region of the handpiece according to FIG. 9, in axial section, and in an illustration to an enlarged scale.

The treatment instrument, designated in its entirety by 1 in FIG. 1, consists of a rearward instrument part, namely a so-called connection part 2, and a forward instrument part, namely the so-called handpiece 3, which are releasably connected with one another by means of a plug-in coupling 4, in particular a plug-in/turn coupling. In the case of the present exemplary embodiment there is arranged at the forward end of the treatment instrument 1 a holder device 5 for a tool 6, whereby the tool 6 may stand out forwardly or to the side. The handpiece 3 may extend straight, or curved or angled towards the side away from the tool 6. The plug-in/turn coupling is formed by means of a coupling recess 7, round in cross-section, and a coupling pin 8 which can be inserted therein with small play for movement. In the case of the present exemplary embodiment, the coupling recess 7 is arranged in the rearward end of the handpiece 3, and the in substance cylindrical pin 8 extends from the connection part 2 forwardly. In the coupled condition the coupling recess 7 and the coupling pin 8 are releasably latched with one another by means of a latching device 9. This has a latching element 9a which is radially movably mounted in the one coupling part and is biassed by means of a spring force into a latching position, crossing the dividing gap, in which the latching element 9a engages into a ring groove in the other coupling part. Such a latching device 9 can be overcome by means of a manual exercise of axial pulling force, whereby the latching element 9a is self-actingly forced into its release position.

The connection part 2 is connected with a flexible supply line 2a, which is connected with a non-illustrated control apparatus. The handpiece 3 is preferably freely rotatable mounted on the coupling pin 8, through which handling is improved. Through the plug-in/turn coupling 4 there extends at least one media line 10 for a treatment or drive medium, e.g. water, compressed air or a water/air mixture (spray). The media line 10 may extend axially (not illustrated) or in a Z-shape through a radial (not illustrated) or hollow cylindrical dividing gap between the coupling recess 7 and the coupling pin 8, whereby the media line 10 passes through the dividing gap in the region of a ring groove in the coupling pin 8 or in the coupling recess 7, so that in any rotational position media throughflow is ensured. To both sides of the through passage the dividing gap is sealed off by means of a sealing ring 8a, which may be arranged in a ring groove in the wall of the coupling recess 7 or in the outer surface of the coupling pin 8. Through this a free rotatability through 360E and more is ensured. The media line 10 extends from the rearward end of the treatment instrument 1 to its forward end region, whereby it may partly run as a channel in the instrument body or as a tube or pipeline. The media line 10 opens out in the forward end region of the treatment instrument 1, out of this treatment instrument, whereby this outlet opening 10a is directed towards the treatment site or towards the tip of the tool 6.

In the case of all exemplary embodiments of the invention, for which the same or similar parts are provided with the same reference signs, the handpiece 3 has a rotary part 12 rotatably mounted therein in a roller bearing. In the case of the exemplary embodiment according to FIG. 1, there is involved a so-called turbine handpiece having an angled shaft 13. This may be formed in one piece or consist of a rearward or forward shaft section 13a, 13b which are fixedly connected with one another at the apex point of the angle. At the forward end of the shaft 13 there is located a thickened head 14 in which a turbine is arranged with a turbine wheel 15 which is mounted rotatably in the head 14 around an axis of rotation 16 extending transversely of the shaft 13 or of its longitudinal middle axis 13c and in the plane of the angle of the shaft 13. The turbine wheel 15 is located in a turbine chamber 17 into which a media line 10b for compressed air opens out and is directed towards the blades of the turbine wheel 15. The turbine wheel 15 is connected with the holder device 5, here with a receiving sleeve 18, into which the tool 6 can be inserted with its shaft and can be releasably fixed in a manner known per se by means of a fixing device. The turbine wheel and the receiving sleeve 18 may be formed in one piece. With the exemplary embodiment in FIG. 1, the turbine wheel 15 is connected with the receiving sleeve 18, at the end thereof away from the insertion opening 18a. For the rotary mounting of the turbine rotor 15a consisting of the turbine wheel 15 and the receiving sleeve 18 there is provided a two-row roller bearing 21 having roller bodies 22, e.g. balls, arranged in two rows, the hollow cylindrical outer bearing sleeve 23 of which sits in a transverse bore 24 in the head 14 and the hollow cylindrical inner bearing sleeve 25 of which sits on the receiving sleeve 18. There is involved, with regard to the turbine wheel 15, a rotational bearing arranged one-sided and to the tool side. On the side of the turbine wheel 15 away from the tool side the turbine rotor 15a is not mounted. The bearing sleeves 23, 25 have on their inner or outer surfaces in each case in the associated transverse plane of the row, raceways 22a in which the roller bodies 22 can circulate. Between the turbine chamber 17 and the transverse bore 24 there is provided a ring seal for the sealing off of the roller bearing 21, which for reasons of simplification is not illustrated. On the side of the turbine wheel 15 away from the tool side, the turbine chamber 17 is covered over by means of a radial head wall 14a. This head wall 14a may be a special component which is connected in the form of a housing 14b with the head housing surrounding the turbine chamber 17 and the transverse bore 24, e.g. is screwed thereto. The shaft of the tool 6 located in the receiving sleeve 18 may be releasable from the side of the head 14 away from the tool side through a coaxial hole with a release pin 26 arranged on this head side. The release pin 26 is mounted displaceably between an extended standby position and a retracted release end position longitudinally of the axis of rotation 16 and biassed for example by means of a spring mounted between the head wall 14*a* and a pin flange 26*a* into its standby position and axially fixed in this position. Such a release device is per se known.

The exemplary embodiments of the roller bearing 11 according to FIGS. 2 to 4 differ from the above-described exemplary embodiment in that either the outer bearing sleeve (FIG. 2) or the inner bearing sleeve (FIG. 3) consist in each case of two outer bearing sleeve parts 23*a*, 23*b* or inner bearing sleeve parts 25*a*, 25*b* arranged behind one another, whereby the bearing sleeve parts may have an axial spacing from one another or, as FIG. 4 shows for an inner bearing sleeve 25, bear on one another. With the configuration according to FIG. 4 it is also possible to allow the raceways 22*a* to open out in each case to the common dividing gap 25*c*, as is schematically illustrated in FIG. 4 by chain lines. A common dividing gap and/or axially running out raceways may also be arranged preferably symmetrically in the outer bearing sleeve 23. With this configuration the outer or inner bearing sleeve parts concerned can be installed by means of an axial movement and in each case completed to the roller bearing 21. With all exemplary embodiments in accordance with FIGS. 2 to 4 it is also possible to identically form outer or inner bearing sleeve parts 23*a*, 23*b* or 25*a*, 25*b* belonging to one another, through which the production costs can be substantially reduced. Depending on the direction of the desired axial support for the roller bearing 11, the bearing sleeve parts 23*a*, 23*b*, 25*a*, 25*b* can be mounted in orientations similar to one another or in positions rotated from one another by 180E.

With the exemplary embodiment according to FIG. 5, the roller bodies 22 of the one row are arranged between surfaces of the outer or of the inner bearing sleeve 23, or sleeve parts 23*a*, 23*b*, 25*a*, 25*b*, of which at least the axial outer surface or both surfaces are arranged on radial flanges 23*c*, 25*c* of the outer bearing sleeve 23 and of the inner bearing sleeve 25, in each case in a raceway 22*b* in the end surfaces of the flanges 23*c*, 25*c* axially facing one another. With the illustrated configuration the inner flange 23*c* extending from the outer bearing sleeve 23 radially inwardly is arranged axially outwardly of the row concerned, and the outer flange 25*c* extending radially outwardly from the inner bearing sleeve 25 is arranged between the rows. The reverse arrangement is also possible, with which the inner flange 23*c* is arranged between the rows, and the outer flange 25*c* is arranged axially outwardly of the row concerned, as is shown in FIG. 6. It is further also possible to arrange the roller bodies 22 and the associated raceways 22*b* in the end face of the shorter outer or inner bearing sleeve 23, 25 and the axially oppositely lying flange 23*c*, 25*c*. That is, there need be present in each case only one flange 23*c* or 25*c*.

Such a roller bearing 21 is with regard to one roller bearing row a radial bearing and with regard to the other roller bearing row an axial bearing. Thus with this configuration the roller bearing 21 can take up both radial and also axial bearing forces. It is suitable in particular for the mounting of a receiving sleeve 18 in the head 14 which in functional operation is loaded not only by radial forces resulting from the resistance forces of the tool 6, but also axial forces in functional operation.

With the exemplary embodiment in accordance with FIG. 7, a roller bearing 21 having the configuration according to FIG. 5 is arranged on the side of the turbine wheel 15 away from the tool side, for mounting the receiving sleeve 18. In combination with a two-row roller bearing 21 on the tool side, this bearing arrangement is particularly advantageous. It is however also possible to arrange the roller bearing 21 according to FIG. 5 or 6 on the tool side of the turbine wheel 15 in the case of a receiving sleeve in accordance with FIG. 1, e.g. in combination with a single-row roller bearing which may be arranged on the side of the turbine wheel 15 away from the tool side in the case of a receiving sleeve 18 in accordance with FIG. 7. With the configuration in accordance with FIG. 7 there is provided another, non-illustrated, tool release device.

With the exemplary embodiment in accordance with FIGS. 8 and 9 the roller bearing 21 is arranged in the shaft 13 for the rotational mounting of a rotary part 12 mounted rotatably therein, here for the rotatable mounting of a drive shaft longitudinal section. With this treatment instrument, a drive motor (not illustrated) is arranged in the extended connection part 2 indicated by chain lines and is drivingly connected by means of a drive shaft chain 33 having a plurality of drive shaft sections with the receiving sleeve 18. In the region of the plug-in coupling 4, the drive shaft chain 33 has a plug-in coupling 32 with two plug-in coupling elements 32*a*, 32*b* which correspond with one another in a form-fitting manner, through which upon coupling and decoupling of the plug-in coupling 4 at the same time a coupling and decoupling of the plug-in coupling 32 is possible.

A drive shaft section 33*a* arranged in the rearward end region of the handpiece 3 extends up into the apex region of the angled shaft 13, its forward end being connected drivingly with a third drive shaft section 33*c* by means of a second drive shaft section 33*b* extending axially in substance only in the apex region, which third drive shaft section extends in the forward shaft section 13*b* up to the receiving sleeve 18 and is drivingly connected with this. For the connection of the drive shaft sections 33*a*, 33*b*, 33*c* there is provided in each case a gear transmission. At the forward end of the first drive shaft section 33*a* there is arranged a gear 34 having inner gear toothing, which engages with a pinion 35 at the rearward end of the second drive shaft section 33*b*. Thereby, the second drive shaft section 33*b* is arranged in the apex region offset towards the side away from the tool 6, whereby at the forward end of the second drive shaft section 33*b* and at the rearward end of the third drive shaft section 33*c* there is arranged in each case a pinion 36, 37 is substance in a transverse plane or arranged overlapping one another, in the sense of spur gears which mesh with one another. The second and the third drive shaft section 33*b*, 33*c* include an obtuse angle W1 which is open towards the side away from the tool 6.

The drive connection between the third drive shaft section 33*c* and the receiving sleeve 18 is formed by means of an angled gear transmission having a conical gear 38 at the forward end of the third drive shaft section 33*c* and conical gear 39 on the receiving sleeve 18. The tooth meshing between the conical gear wheels 38, 39 is arranged, with regard to the third drive shaft section 33*c*, on its side away from the tool 6. Through this the receiving sleeve 18 is driven in the same direction of rotation as the first drive shaft section 33*a*. The receiving sleeve 18 is rotatably mounted by means of two roller bearings 41, 42 in the head 14, which roller bearings have a spacing from one another directed longitudinally of the axis of rotation 16, which spacing is larger than the conical gear 38, so that the latter can be arranged therebetween, inclusive of the conical gear 39 which is arranged on the side of the conical gear 38 away from the tool 6 and at the same time on the side of roller bearing 41 towards the tool 6, which roller bearing is arranged more distant from the tool 6 than the other roller bearing 42. For rotational mounting of the second drive shaft section 33c there is provided on the end sections of this drive shaft section 33c in each case a roller bearing 33, 44, the outer rings of which sit in a non-illustrated longitudinal hole of the shaft section 13b.

The configuration of the gear 34 as a hollow wheel makes possible, with a radially small construction, a relatively great gearing up of the speed of rotation between the first and the second drive shaft section 33a, 33b.

With the exemplary embodiment in accordance with FIG. 8 there are provided for the mounting of the first drive shaft section 33a and of the second drive shaft section 33b in each case in the shaft 13 a two-row roller bearing 21a, 21b. This roller bearing 21a, 21b is sufficient in each case to mount to the overall drive shaft section 33a or 33b sufficiently stably. The first drive shaft section 33a rearwardly projects beyond the roller bearing 21a freely standing out, through which a slight radial flexibility is present for the coupling with the drive shaft section of the connection part 2. For increasing the flexibility there may be connected between the first drive shaft section 33a and the gear 34 a joint connection 28 having a transverse pin 29, through which the radial flexibility of the first drive shaft section 33a is increased. The gear 34 consists of a rearward cylindrical or hollow cylindrical bearing section 34a, on the forward end of which a flange 34b is arranged which carries at its forward side the hollow gear crown. In the exemplary embodiment, the roller bearings 21a, 21b are of the configuration according to FIG. 3.

With all roller bearings 21, 21a, 21b the spacing a of the roller body rows from one another may preferably be greater than the mean diameters b of the roller body raceways 22a. The roller bearing 21b is so long, see L, that it fits between the pinion 35, 36 through which at the same time an axial limiting for the second drive shaft section 32b is constituted. With the exemplary embodiments according to FIGS. 5 and 6, the spacing a can also be smaller than the mean raceway diameter b, since radially only one roller body row is effective.

Both roller bearings 21a, 21 are preferably mounted in a common carrier body 44 which sits in the shaft 13 in the region of the rearward shaft section 13a neighbouring the apex point, and by means of a rearwardly or forwardly opening receiving hole is mountable from the rear and again demountable from the rear, or vice versa, and is axially fixable in a non-illustrated manner.

As can further be understood from FIG. 8, the rearward roller bearing 21a is inserted from the rear into a receiving hole 45a of the carrier body 45 and for example by means of a flange 23d arranged on the rearward end of the outer bearing sleeve 23 axially fixed towards the fore. The forward roller bearing 21b is, in contrast, inserted from the fore into a receiving hole 46 of the carrier body 45 and axially fixed. The flange 34 is mounted with play for movement in the receiving hole 45a between the roller bearing 21a and the bottom of the receiving hole 45a.

47 designates a light conductor rod which in vicinity of the edge of the shaft 13 extends in the shaft from the rear forwardly to the exit window 48 directed to the free end of the tool 6. In functional operation of this handpiece 3 light from a light source is coupled into the light conductor rod 47, whereby the light source 47a is arranged on a rotatably mounted carousel 49 (schematically indicated) in the connection part 2, so that also in this case the free rotatability of the handpiece 3 in the plug-in/turn coupling 4 is ensured.

The angle W2 included in FIG. 8 between the middle axis of the forward shaft section 13b and the axis of rotation 16 of the receiving sleeve 18 is in substance 100E. Such a configuration is, taking into account the anatomy of the mouth of a patient, particularly favourable. This favourable configuration with the angle W2 equal to 100E applies not only for the handpiece 3 according to FIG. 8 operable with a motor in connection part 2, but also for the turbine handpiece 3 in accordance with FIG. 1 and the handpiece 3 in accordance with FIG. 9 which is still to be described, having a motor in the connection part 2, even though the latter are shown with an angle W3 between the shaft section 13b and the axis of rotation 16 of about 90E. An angle between 90 and preferably 100E is favourable.

The handpiece 3 according to the exemplary embodiment in accordance with FIG. 9 differs from the exemplary embodiment according to FIG. 8 in two main respects. On the one hand, the second and the third drive shaft section 33b, 33c are not arranged to overlap but their ends directed towards one another axially neighbour one another, whereby an obtuse angle W4 is included which is lesser than the angle W1 and is about 135 to 150E. The gears 36, 37 thus mesh in the sense of a real angled transmission with forwardly and rearwardly directed teeth, which in each case are arranged on the side of the periphery away from the tool 6. Thus, the direction of rotation of the second and of the third drive shaft section 33b, 33c, are not counter to one another, as with the exemplary embodiment according to FIG. 8, but in the same sense as one another.

In contrast to the exemplary embodiment according to FIG. 8, with the exemplary embodiment according to FIGS. 9 and 10 the second drive shaft section 33b is not arranged axis parallel with regard to the first drive shaft section 33a, but it includes therewith an acute angle W5 of about 10 to 20E. Further, the second drive shaft section 33b is arranged with the roller bearing 21b in a hollow cylindrical mounting sleeve 51 which can be inserted into, in particular screwed into, the bearing body 44 from the fore and with the pinion 35, preferably formed in one piece on the second drive shaft section 33b, the gear 36 and the roller bearing 21b, constitutes a prefabricatable structural unit.

As FIG. 10 shows, the rearward end of the third drive shaft section 33c can be mounted with the roller bearing 43 in a bearing sleeve 53 which projects in one piece from the rearward shaft section 13a into the forward shaft section 13b and in the transition region has an enlarged free chamber 44 for the gear 36 or also for the mounting sleeve 52.

On the other hand, with the exemplary embodiment according to FIG. 9, the drive connection between the conical gears 38, 39 is arranged not on the side away from the tool 6 but on the side towards the tool 6 of the conical gear 38, whereby the conical gear 39 is arranged, with reference to the conical gear 38, on the receiving sleeve 18 on the side towards the tool 6. Through this, in comparison with the configuration according to FIG. 8, the direction of rotation of the receiving sleeve 18 is reversed, whereby the above-described reversal of direction of rotation at the gear transmission 35, 37 is compensated and thus the directions of rotation of the receiving sleeves 18 are again the same with the exemplary embodiments according to FIGS. 8 and 9.

As FIG. 11 further shows, the receiving sleeve 18 is mounted in the head 14 in a two-row roller bearing 21c, which likewise corresponds to the configuration according to FIG. 3, that is, has a through-going outer bearing sleeve 23. The conical gear 39 can be with a hollow cylindrical section carrier of the associated inner bearing sleeve section 25b. In the end region of the receiving sleeve 18 away from the tool 6, which end region carries the associated inner bearing sleeve section 25a, there is axially displaceably mounted an additional release pin 26b for spreading a mounting sleeve 55 arranged in the receiving sleeve 18, and is manually actuable by means of the release pin 26a from the side away from the tool 6. The end of the outer bearing sleeve 23 away from the tool 6 can be mounted in the screw support 14c of the head housing cover 14c having the head wall 14b, as FIG. 11 shows. The roller bearing 21c is thus likewise mountable and demountable from the side away from the tool 6. For the through engagement of the third drive shaft section 33c, the outer bearing sleeve 23 has at the relevant side a through-hole 23e. In order to avoid a rotation of the outer bearing sleeve 23 there is provided a rotary fixing for this, which for example may be formed by means of a cam 56 which engages in a recess 57. With the exemplary embodiment, the cam 56 is arranged in the end region away from the tool on the periphery of the outer bearing sleeve 23 and it engages into an axial groove in the wall of the bearing bore receiving the outer bearing sleeve 23. With this configuration, the rotary part 12 is thus constituted by means of the receiving sleeve 18.

With all exemplary embodiments there are provided cages associated with the roller bodies 22 between the outer bearing sleeve 23 and the inner bearing sleeve 25 or the sleeve parts 23a, 23b, 25a, 25b.

The invention claimed is:

1. Medical or dental-medical handpiece having a forward end region and comprising a rotary part and at least one roller bearing provided for mounting the rotary part, and at least two roller body rows having a mean diameter b disposed adjacent to each other between inner and outer rings, wherein the roller bearing has roller bodies disposed in two roller body rows and spaced from each other at an axial spacing a, the outer ring extends axially over the two roller body rows, and the inner ring comprises two ring parts disposed axially behind each other, wherein the ring parts are axially spaced from each other.

2. Handpiece of claim 1, wherein the axial spacing a is greater than the mean diameter b of the roller bodies in at least one row.

3. Handpiece of claim 1, wherein the roller bearing is disposed in the forward end region of the handpiece and mounts at least one of a turbine rotor and a receiving sleeve for a tool.

4. Handpiece of claim 3, wherein the turbine rotor includes a turbine wheel and only one roller bearing is disposed on one side of the turbine wheel.

5. Handpiece of claim 4, wherein the turbine wheel has a tool side and the roller bearing is disposed on the tool side of the turbine wheel.

6. Handpiece of claim 4, wherein the handpiece includes a forward drive shaft section, the rotary part is formed by a receiving sleeve for a tool, and the forward drive shaft section of the handpiece penetrates a through-hole defined in the outer ring and has a conical gear at a forward end which is in driving connection with a conical gear arranged on the receiving sleeve.

7. Handpiece of claim 1, wherein the roller bearing is disposed in the handpiece for mounting at least one end of a drive shaft section.

* * * * *